United States Patent
Rosenthal

[11] Patent Number: 6,134,458
[45] Date of Patent: Oct. 17, 2000

[54] LIGHT PROBE FOR A NEAR-INFRARED BODY CHEMISTRY MEASUREMENT INSTRUMENT

[75] Inventor: Robert D. Rosenthal, Gaithersburg, Md.

[73] Assignee: Futrex Inc., Gaithersburg, Md.

[21] Appl. No.: 09/210,950

[22] Filed: Dec. 15, 1998

[51] Int. Cl.[7] ....................................... A61B 5/00
[52] U.S. Cl. ........................................... 600/310; 600/322
[58] Field of Search .................................. 600/310, 316, 600/322, 323, 340, 344, 473

[56] References Cited

U.S. PATENT DOCUMENTS

| | | | |
|---|---|---|---|
| 5,497,769 | 3/1996 | Gratton et al. | 600/323 |
| 5,497,771 | 3/1996 | Rosenheimer | 600/323 |
| 5,533,509 | 7/1996 | Koashi et al. | 600/316 |
| 5,632,273 | 5/1997 | Suzuki | 600/310 |
| 5,769,076 | 6/1998 | Maekawa et al. | 600/322 |
| 5,807,248 | 9/1998 | Mills | 600/322 |
| 6,006,119 | 12/1999 | Soller et al. | 600/322 |

Primary Examiner—Eric F. Winakur
Assistant Examiner—Joseph A. Cadugan
Attorney, Agent, or Firm—Rothwell, Figg, Ernst & Manbeck

[57] ABSTRACT

A light probe method and apparatus is provided for an infrared body chemistry measurement instrument. The light probe includes an illumination ring of a light-conducting material, having facets on an exterior circumferential surface, and an inner circumferential surface at about a forty-five degree angle, infrared light emitting devices positioned at each facet, a coaxially located optical detector, a shielding ring coaxially located between the optical detector and the illumination ring, and a cover having a central opening which exposes the optical detector, the shielding ring, and the illumination ring, wherein a length dimension of the light probe is less than a diameter dimension. The method includes radially illuminating an illumination ring with infrared light, redirecting the infrared light to an axial direction perpendicular to the radially inward direction, conducting the infrared light through the illumination ring and into a body part under test, and receiving reflected and scattered light in an optical detector concentric with the illumination ring.

29 Claims, 3 Drawing Sheets

VIEW A-A

LIGHT PROBE FOR A NEAR-INFRARED BODY CHEMISTRY MEASUREMENT INSTRUMENT

BACKGROUND OF THE INVENTION

1. Field of the Invention

The present invention relates to a new and improved light probe for a near-infrared body chemistry measurement instrument.

2. Description of Background Art

Body chemistry measurement is a health field wherein the goal is to detect, monitor, or prevent health problems due to disease, illness, or genetic propensity by measuring analytes in the body. A large and important area of interest is in developing measurement devices that are inexpensive to produce, yet give fast and reliable results. The ultimate goal is an instrument that is reliable enough for medical use, yet inexpensive and reliable enough for use by ordinary persons. Through the use of such body chemistry measurement instruments, persons will be able to monitor their own health.

Several body chemistry characteristics are vital to long term health, and are becoming easier to monitor. These are characteristics such as body fat percentage and body water percentage. Long term health can be improved by keeping both characteristics within widely-accepted ranges. It is well established that health risks increase for those who are more than twenty percent over optimal weight. Measurement of weight alone, however, is not sufficient. Body composition (i.e., body fat levels), is one preferred measure of health and fitness. Generally, body fat levels of fifteen to eighteen percent for men and twenty to twenty-five percent for women are considered acceptable. Body fat levels greater than twenty-six percent for men and twenty-nine percent for women are considered to be indicative of obesity and are a potential risk factor for the development of diseases such as cardiovascular disease, high blood pressure, and diabetes. Other important body function characteristics that often require regular measurement are blood pressure, pulse rate, blood glucose levels, etc.

Body fat testing can be measured by several known methods, such as by measurement of body part circumferences, water immersion, bioelectrical impedance, or infrared light interactance.

Each of the above measurements has particular problems or disadvantages. Measuring body part circumferences and using body fat calipers are two easy and cheap methods, but may be inaccurate due to a user's lack of knowledge on proper use, and may further suffer from differences between individuals, differences due to age, or differences due to gender. Numerous combinations of skinfold measurements taken at different sites are required. This data must be applied to regression equations to predict body fat levels.

Water immersion body fat testing is widely accepted as the standard by which other body fat testing methods are measured. A person is immersed in water and the volume of displaced water is compared to the person's weight. Water immersion tests are expensive, somewhat complicated, require relatively expensive and bulky equipment, and must be performed by trained personnel. These limitations make it impractical for general use.

Body fat composition may be measured by bioelectrical impedance, where body fat is indirectly measured by measuring the body's resistance to a small electrical current. This resistance is used to obtain body fat levels, as bones, muscle and tissue have a high level of electrical conductivity compared to body fat. In principle, the lower the electrical impedance, the greater an individual's lean body mass. This method can be incorporated into a testing device that is small and inexpensive, and available for general use. However, the accuracy of the bioelectrical impedance method can be affected by several critical factors. To make a valid measurement, the subject must be in a stable condition. The amount of hydration (i.e., the amount of water in the body) and the amount of electrolytes must be consistent every time a measurement is made. This is because bioelectrical impedance does not measure body fat, it measures the body's resistance to electrical current flow. Thus, for example, if the person is perspiring, the test results of the predicted body fat may be inaccurate. In fact, in order to obtain accurate measurements, the National Institutes of Health (NIH) insists that the person being tested with a bioelectrical impedance instrument have fasted (no food or drink) for a minimum of four hours, and preferably six hours.

Near-infrared interactance measures body fat levels by measuring the absorption of infrared light at very specific wavelengths. All organic materials (i.e., fat or protein) absorb light in unique parts of the infrared light spectrum. Body fat can therefore be accurately and quickly measured by directing selected wavelengths of infrared or near-infrared light into a test area and measuring the amount of reflected light. Hereinafter, the term "infrared" will be used to encompass infrared as well as near-infrared wavelengths. Body fat will absorb the infrared light, while lean body mass will reflect it. Infrared light measurement instruments may also be used for other body chemistry measurements, such as blood analytes (e.g., glucose, hemoglobin), percentage of muscle (i.e., protein), pulse rate, etc.

In operation, a long narrow light probe wand is connected to the infrared measurement instrument, with the light probe wand both emitting the infrared light and sensing the reflected light. The light probe wand must be used properly to avoid introducing errors into the measurement, as the operator may place the operative end of the light probe wand in a poor measurement site on the test subject or may apply an improper or inconsistent pressure on the light probe wand.

The relatively large ratio between the light probe wand length in relation to its diameter presents a problem of incorporating a light probe into measurement equipment. Automated test instruments for measurements such as blood pressure are commonly available, and are popular due to their ease of use. They commonly use a cuff in which a person inserts his or her upper arm for testing. It has been found that the biceps or triceps muscles of the upper arm are good locations for infrared measurement of body fat levels. An infrared measurement employing a relatively thin, disc-shaped light probe could be easily incorporated into an existing automated measurement instrument. It is desirable to have an infrared light probe of a size and dimension that could be used in a pressure cuff, such as in a blood pressure tester, and would therefore be easy to use, consistent, and capable of being used without the help or expense of trained personnel. An infrared light probe could therefore be included as part of a blood pressure tester or other automated body chemistry measurement.

What is needed, therefore, is a light probe method and apparatus of a small depth dimension that can be used for an infrared body chemistry measurement instrument.

SUMMARY OF THE INVENTION

It is therefore an object of the invention to provide a new and improved light probe for a body chemistry measurement instrument.

It is another object of the invention to provide a light probe for a body chemistry measurement instrument with a low length to diameter ratio.

It is yet another object of the invention to provide a light probe for a body chemistry measurement instrument wherein the infrared light is conducted onto the test subject via an illumination ring.

It is yet another object of the invention to provide a light probe for a body chemistry measurement instrument wherein the infrared light enters the illumination ring from a radially inward direction.

It is yet another object of the invention to provide a light probe for a body chemistry measurement instrument wherein the illumination ring redirects the infrared light from a radially inward direction to an axial direction.

A light probe for a near-infrared measurement instrument is provided according to a first aspect of the invention. The light probe comprises an illumination ring of a light-conducting material, having a plurality of facets on an exterior circumferential surface and having an inner circumferential surface at about a forty-five degree angle, wherein infrared light radially entering the illumination ring from one of the plurality of facets is redirected by the inner circumferential surface in a radially perpendicular direction, a plurality of infrared light emitting devices positioned at each facet of the plurality of facets and capable of emitting the infrared light into the plurality of facets of the illumination ring, an optical detector coaxially located with the illumination ring, a shielding ring coaxially located between the optical detector and the illumination ring, and capable of preventing the infrared light from passing radially from the illumination ring to the optical detector, and a cover for enclosing a combination of the illumination ring, the plurality of infrared light emitting devices, the optical detector, and the shielding ring, with said cover having a central opening which exposes the optical detector, the shielding ring, and the illumination ring, wherein a length dimension of said light probe is less than a diameter dimension.

A light probe for a near-infrared measurement instrument is provided according to a second aspect of the invention. The light probe comprises an illumination ring of a light-transmitting material, having a plurality of facets on an exterior circumferential surface, a plurality of infrared light emitting devices positioned at each facet of the plurality of facets and capable of emitting the infrared light into the plurality of facets of the illumination ring, an optical detector coaxially located with the illumination ring, a shielding ring coaxially located between the optical detector and the illumination ring, and capable of preventing the infrared light from passing directly from the illumination ring to the optical detector, and having an outer circumferential surface at about a forty-five degree angle, wherein the infrared light radially conducted through the illumination ring to the outer circumferential surface of the shielding ring is redirected by the outer circumferential surface in a radially perpendicular direction, and a cover for enclosing a combination of the illumination ring, the plurality of infrared light emitting devices, the optical detector, and the shielding ring, with said cover having a central opening which exposes the optical detector, the shielding ring, and the illumination ring, wherein a length dimension of said light probe is less than a diameter dimension.

A method for illuminating a body part with an infrared light probe having a small length dimension is provided according to a third aspect of the invention. The method comprises the steps of radially illuminating an illumination ring with infrared light, redirecting the infrared light to an axial direction perpendicular to the radially inward direction, conducting the infrared light through the illumination ring and into a body part under test, and receiving reflected and scattered light in an optical detector concentric with the illumination ring.

The above and other objects, features and advantages of the present invention will become clear from the following description of the preferred embodiment thereof, taken in conjunction with the accompanying drawings.

DETAILED DESCRIPTION OF THE PREFERRED EMBODIMENTS

Figure 1:
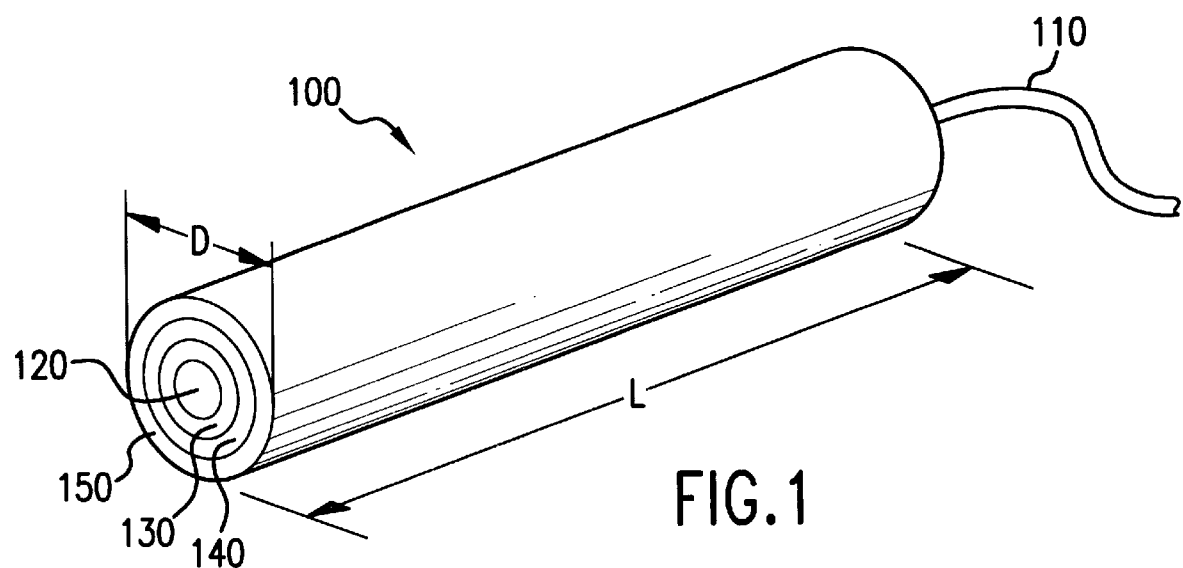
FIG. 1 shows a infrared light probe of the prior art.

Referring now to FIG. 1, there is shown a wand-type light probe 100 of the prior art. The prior art light probe 100 includes a cord 110 for connecting the prior art light probe 100 to a measurement instrument (not shown), an optical detector 120, a shielding ring 130, an illumination ring 140, and a cover 150. As can be seen from the drawing, the prior art light probe 100 has a high length (L) to diameter (D) ratio. Typical L/D ratios in the prior art are on the order of five or greater. Although the prior art light probe 100 performs its function, it is not dimensionally or physically well-suited for automated measurement instruments. One such instrument is the automated blood pressure measurement instrument commonly found in pharmacies and drugstores, wherein ordinary persons can insert an arm in a cuff and press a button to start the measurement. The machine automatically inflates the cuff, senses blood pressure and pulse rate, releases the cuff, and displays blood pressure and pulse rate readings. This machine could be readily used for other body chemistry tests by incorporating an infrared interactance measurement instrument. The infrared instrument could be easily incorporated if a light probe could be fitted in the cuff without size problems.

Figure 2:
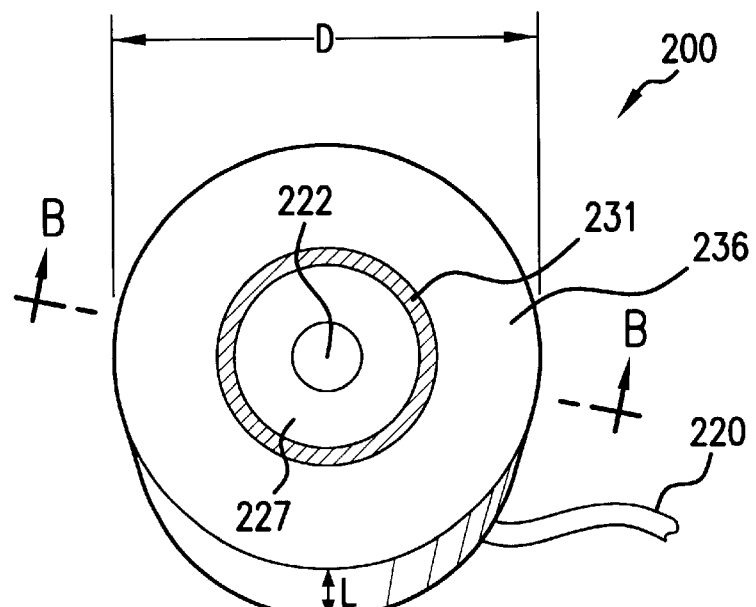
FIG. 2 shows the light probe of the present invention.

FIG. 2 shows a new and improved light probe 200 of the present invention having a very low length to diameter (L/D) ratio. The light probe 200 comprises a cord 220 for connecting to a measurement instrument (not shown), an optical detector 222, a shielding ring 227, an illumination ring 231, and a cover 236. Due to the design, function and positioning of the internal components, the light probe 200 of the present invention has a very low length to diameter (L/D) ratio. The light probe 200 is geometrically similar to the typical blood pressure sensor built into blood pressure cuffs. The shape of the light probe 200 therefore allows it to be used in an automated instrument or in a hand-held manner.

The infrared light used for body chemistry measurement is emitted from the illumination ring 231 into the test subject. The light probe 200 is positioned so that a body part, preferably the biceps or triceps muscle of the upper arm, is pressed against the illumination ring 231 and the optical detector 222. The shielding ring 227 prevents infrared light from traveling directly from the illumination ring 231 to the optical detector 222 without passing through the test subject. Light from the illumination ring 231 that has been reflected and scattered is received by the optical detector 222.

Figure 3A:
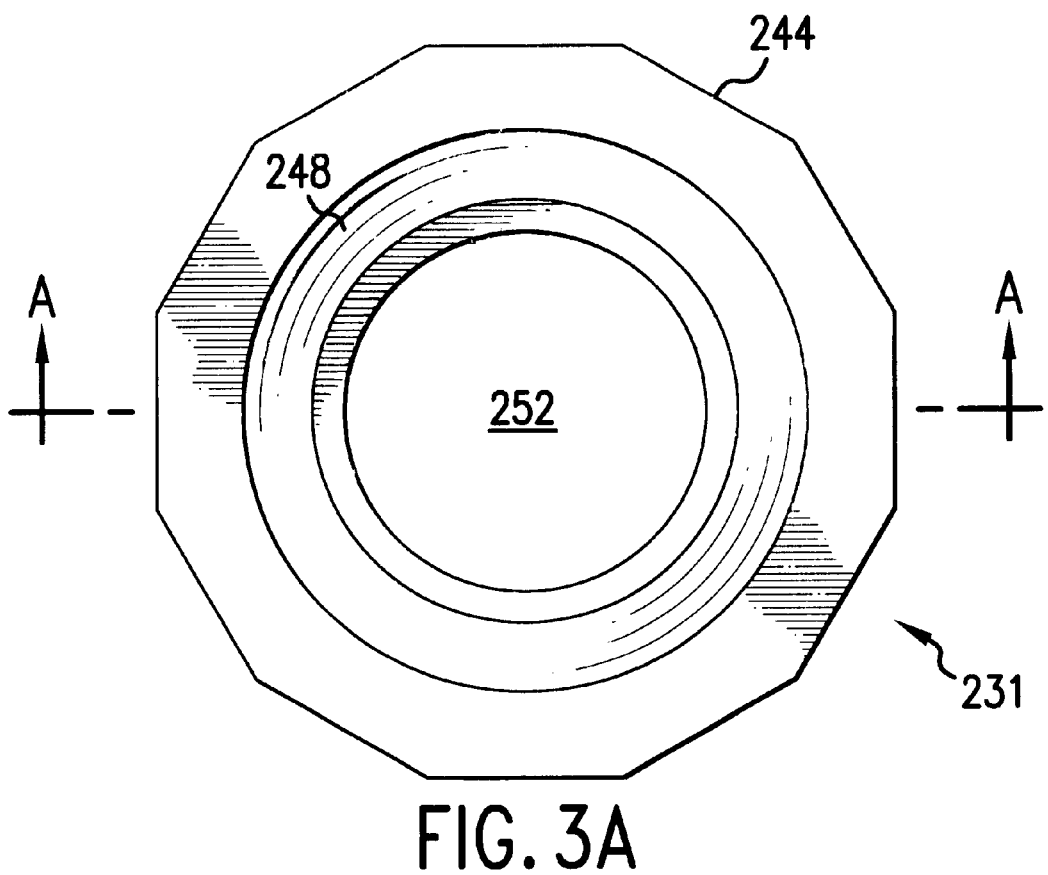
FIGS. 3A and 3B show top and section views respectively of the illumination ring.
Figure 3B:
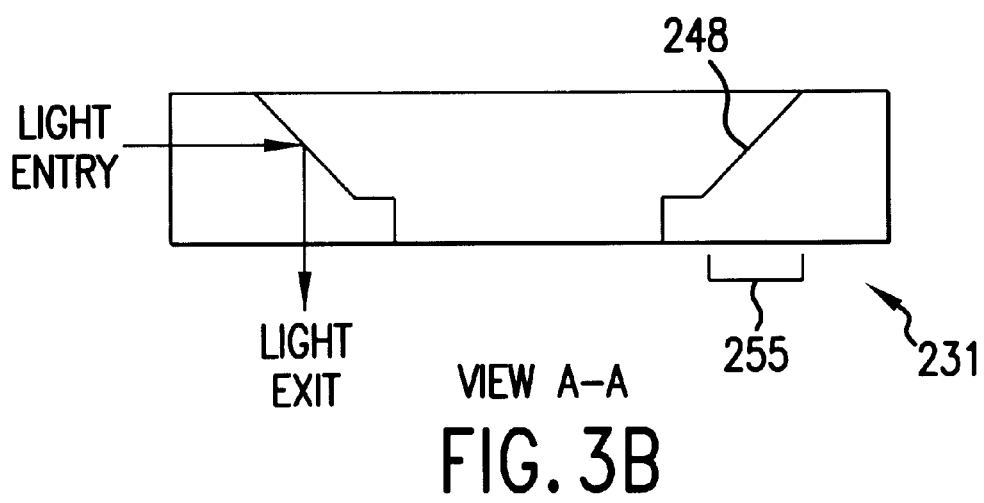

FIG. 3A is a top view of the illumination ring 231. The illumination ring 231 further includes an angled surface 248 (as best shown in FIG. 3B) and a central opening 252. The angled surface 248 is the area of the illumination ring 231 that is exposed and communicates with the body part under test. The illumination ring 231 has on its outer circumferential surface a plurality of facets 244. In the preferred embodiment the illumination ring 231 includes twelve of such aforementioned facets 244. In the preferred embodiment, the twelve facets 244 allow the use of six pairs of opposing infrared light emitting devices 400 (see FIGS. 4A–4B and FIGS. 5 and 6) with each pair preferably generating a selected wavelength of infrared light. The facets 244 enable infrared light emitting devices 400 to be positioned around the outer circumferential surface of the illumination ring 231 and direct the infrared light radially inward.

The material of the illumination ring 231 must be translucent and capable of conducting light. In the preferred embodiment, the illumination ring 231 is formed from acrylic. One example of a suitable acrylic material is Plexiglas® #2447.

FIG. 3B is a section view of the illumination ring 231 along the section line A—A of FIG. 3A. FIG. 3B illustrates the angled surface 248. The direction of infrared light entry and exit due to the angled surface 248 can be seen from the arrows in FIG. 3B. In the preferred embodiment, the angled surface 248 is at an angle of forty-five degrees from the horizontal and consequently from the direction of light entry. In the preferred embodiment, the angled surface 248 does not have to be silvered (mirrored), as the angle plus the high refractive index of the acrylic to air boundary causes the entering infrared light to be refracted and as a result the infrared light is redirected in a direction perpendicular to the entry direction (i.e., it is redirected from a radially inward direction to an axial direction). The angled surface 248 can be either molded or machined and polished into the illumination ring 231.

The area labeled with the descriptive numeral 255 is the annular region of the illumination ring 231 (corresponding to the angled surface 248) from which the redirected light emerges.

Figure 4A:
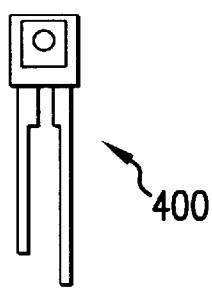
FIGS. 4A and 4B show front and top views of an infrared light emitting device.
Figure 4B:
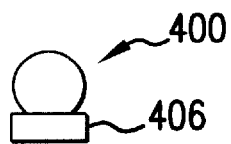

FIGS. 4A and 4B show a typical infrared light emitting device 400 that may be used with the light probe 200 of the present invention. In the preferred embodiment, the infrared light emitting device 400 may be an infrared light emitting diode (IRED or LED) available from Stanley Electronics, part number AN505. Wide beam angle devices are preferred, as they provide nearly uniform illumination around the illumination ring 231. The infrared light emitting device 400 may include a narrow band pass optical filter 406, which may be fastened or attached to the radiating surface of the infrared light emitting device 400. The filter 406 preferably has a band pass characteristic in the desired infrared light range, thereby eliminating all infrared light of wavelengths above and below the desired infrared light wavelength. In addition, the filter 406 may have its edges painted or covered with an opaque material to prevent light leaks. The infrared light emitting device 400 may be attached to all facets 244 of the illumination ring 231, with the light radiating surface positioned radially inward on a facet 244 of the illumination ring 231.

Figure 5:
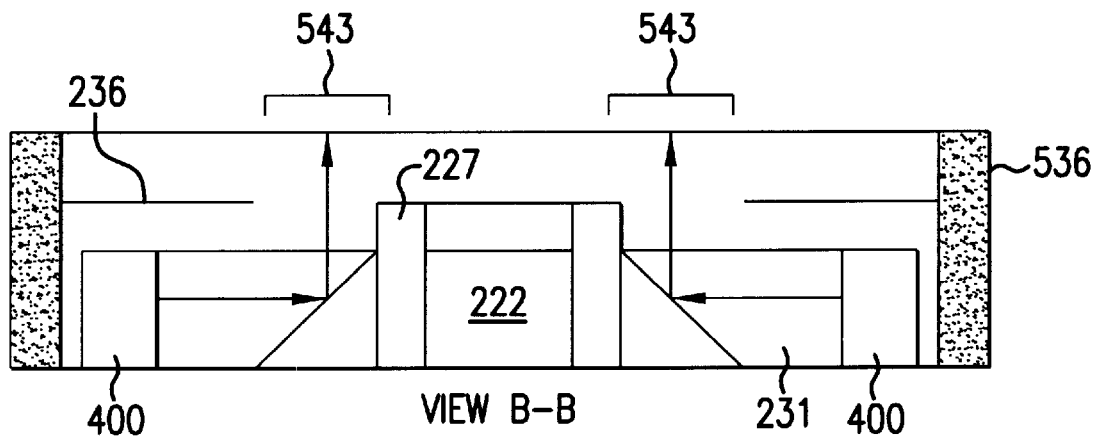
FIG. 5 shows a section view of a first embodiment of the invention.

FIG. 5 shows a section view of a light probe 500 of a first embodiment of the invention along the section line B—B of FIG. 2.

The light probe 500 comprises an optical sensor 222, a shielding ring 227, an illumination ring 231, a plurality of infrared light emitting devices 400, a cover 236, and a compressible ring 536.

The plurality of infrared light emitting devices 400 are positioned at each facet of the illumination ring 231 (see FIG. 3A). Light emitted by the infrared light emitting devices 400 (depicted by arrows in the figure) is redirected by the illumination ring 231 and is allowed to pass through the annular opening 543 defined by the shielding ring 227 and the cover 236. The shielding ring 227 contains the optical detector 222 and prevents light from reaching the optical detector 222 unless the light is reflected or scattered by a body part of a test subject. Not shown are the wires connecting electronic circuits to both the optical detector 222 and the infrared light emitting devices 400. The electronic circuits required for both are well known in the art, and may be incorporated into the light probe 500 or may be incorporated into the measurement instrument. Also shown is the compressible ring 536, which may be optionally included as part of the light probe 500. The compressible ring 536 is positioned around the outer circumference of the light probe 500, and extends above the cover 236 on the light probe face that contacts a body part under test. The compressible ring 536 may be made of a soft opaque foam, which when compressed in use prevents external light from entering the light probe 500.

Figure 6:
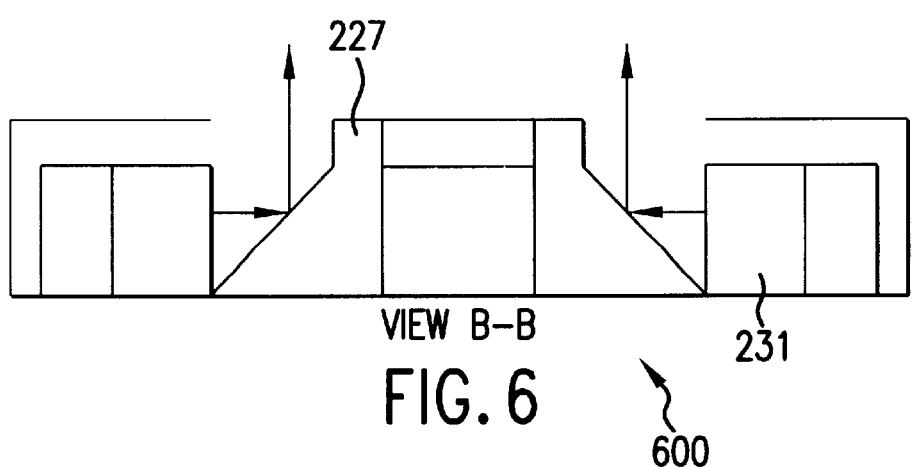
FIG. 6 shows a section view of a second embodiment of the invention.

FIG. 6 shows a section view of a light probe 600 of a second embodiment of the invention along the section line B—B of FIG. 2. In this embodiment, the shape of the illumination ring 231 and the shielding ring 227 are different. The angled surface of the light probe 600 exists on the outer circumferential surface of the shielding ring 227 instead of on the inner circumferential surface of the illumination ring 231. The infrared light passes through the illumination ring 231 in a radially inward direction and is redirected in an axial direction by the shielding ring 227. In this embodiment, the angled surface of the shielding ring 227 may be silvered or may alternatively be made of aluminum having a polished angled surface for redirecting light.

The light probe 200 can be standardized (calibrated) in a manner described in commonly owned U.S. Pat. No. 4,990,772, which is herein incorporated by reference. Alternatively, standardization may be performed by taking advantage of the small amount of infrared light that leaks directly through the angled surface 248 of the illumination ring 231. This small light leakage does not interfere with the measurement. The leaked light can be used to eliminate the need for an external optical standard. Internal standardization is accomplished by positioning a reference optical detector (not shown in the figures) inside the light probe 200 to pick up light leakage. When any infrared light emitting device 400 is activated (before or after the body part is placed on the probe), the leaked light is picked up by the reference optical detector. If the output of the infrared light emitting device 400 has drifted or diminished, a simple correction can be made according to the following equation:

$$E_{M\ CORRECTED} = E_M * (E_{RF}/E_{RN});$$

where $E_{M\ CORRECTED}$ = the value of the measurement of the optical detector 222 after being corrected by the reference detector, $E_M$ = the energy that reaches the optical detector 222 when a body part is placed on the light probe 200, $E_{RF}$=the energy that reached the reference detector at the time the unit was originally calibrated, and $E_{RN}$=the energy that reached the reference detector just prior to or just after the body part is placed on the probe. Therefore, the actual measurement is a ratio of the light that reaches the optical detector 222 after interacting with the body part, to the light captured by the reference detector built into the light probe 200. Multiple reference detectors may be employed if needed. This standardization approach would be highly valuable in a typical automated application where calibration by an external physical optical standard would be very inconvenient.

While the invention has been disclosed in detail above, the invention is not intended to be limited to the invention as disclosed. It is evident that those skilled in the art may now make numerous uses and modifications of and departures from the specific embodiments described herein without departing from the inventive concepts.

What is claimed is:

1. A light probe for an infrared body chemistry measurement instrument, comprising:

an illumination ring of a light-conducting material, having a plurality of facets on an exterior circumferential surface thereof and having an inner circumferential surface at about a forty-five degree angle, wherein light radially entering said illumination ring from one of said plurality of facets is redirected by said inner circumferential surface in a radially perpendicular direction;

a plurality of infrared light emitting devices, each positioned at one of said plurality of facets and capable of emitting infrared light into said plurality of facets of said illumination ring;

an optical detector coaxially located within said illumination ring;

a shielding ring coaxially located between said optical detector and said illumination ring, and capable of preventing said infrared light from passing radially from said illumination ring to said optical detector; and a cover enclosing a combination of said illumination ring, said plurality of infrared light emitting devices, said optical detector, and said shielding ring, with said cover having a central opening which exposes said optical detector, said shielding ring, and said illumination ring, wherein a length dimension of said light probe is less than a diameter dimension.

2. The light probe of claim 1, wherein said illumination ring is made from a translucent acrylic material.

3. The light probe of claim 1, wherein said illumination ring is adapted for redirecting six distinct wavelengths of infrared light.

4. The light probe of claim 1, wherein said plurality of facets comprises twelve facets.

5. The light probe of claim 4, wherein six pairs of said infrared light emitting devices are positioned at said twelve facets, with each pair of said six pairs emitting the same wavelength of said infrared light and said pair being positioned in radially opposing facets.

6. The light probe of claim 1, wherein said infrared light emitting devices are infrared light emitting diodes.

7. The light probe of claim 1, wherein said infrared light emitting devices are wide beam angle infrared light emitting devices.

8. The light probe of claim 1, wherein an infrared light emitting device of said plurality of infrared light emitting devices further includes a narrow band pass optical filter positioned over the radiating surface of said infrared light emitting device to allow only a predetermined wavelength of light to pass through.

9. The light probe of claim 1, wherein said cover further includes a sealing ring of an opaque material fastened to an outermost edge of a face of said cover, with said sealing ring being compressible and preventing outside light from entering said optical detector when a body part under test is pressed against said light probe.

10. A light probe for an infrared body chemistry measurement instrument, comprising:

an illumination ring of a light-transmitting material, having a plurality of facets on an exterior circumferential surface thereof;

a plurality of infrared light emitting devices, each positioned at one of said plurality of facets and capable of emitting infrared light into said plurality of facets of said illumination ring;

an optical detector coaxially located within said illumination ring;

a shielding ring coaxially located between said optical detector and said illumination ring, and capable of preventing said infrared light from passing directly from said illumination ring to said optical detector, and having an outer circumferential surface at about a forty-five degree angle, wherein said infrared light radially conducted through said illumination ring to said outer circumferential surface of said shielding ring is redirected by said outer circumferential surface in a radially perpendicular direction; and a cover enclosing a combination of said illumination ring, said plurality of infrared light emitting devices, said optical detector, and said shielding ring, with said cover having a central opening which exposes said optical detector, said shielding ring, and said illumination ring, wherein a length dimension of said light probe is less than a diameter dimension.

11. The light probe of claim 10, wherein said illumination ring is made from a translucent acrylic material.

12. The light probe of claim 10, wherein said illumination ring is adapted for redirecting six distinct wavelengths of infrared light.

13. The light probe of claim 10, wherein said plurality of facets comprises twelve facets.

14. The light probe of claim 13, wherein six pairs of said infrared light emitting devices are positioned at said twelve facets, with each pair of said six pairs emitting the same wavelength of said infrared light and said pair being positioned in radially opposing facets.

15. The light probe of claim 10, wherein said infrared light emitting devices are infrared light emitting diodes.

16. The light probe of claim 10, wherein said infrared light emitting devices are wide beam angle infrared light emitting devices.

17. The light probe of claim 10, wherein an infrared light emitting device of said plurality of infrared light emitting devices further includes a narrow band pass optical filter positioned over the radiating surface of said infrared light emitting device to allow only a predetermined wavelength of light to pass through.

18. The light probe of claim 10, wherein said cover further includes a sealing ring of an opaque material fastened to an outermost edge of a face of said cover, with said sealing ring being compressible and preventing outside light from entering said optical detector when a body part under test is pressed against said light probe.

19. A method of measuring biochemical analytes by illuminating a body part with an infrared light probe having a small depth dimension, comprising the steps of:

radially illuminating an illumination ring with infrared light in a radially inward direction;

redirecting said infrared light to an axial direction perpendicular to said radially inward direction;

conducting said infrared light through said illumination ring and into a body part under test; and receiving reflected and scattered light in an optical detector concentric with said illumination ring.

20. The method of claim 19, wherein the illuminating step further comprises radially illuminating saia illumination ring with infrared light from a plurality of radially located infrared light emitting devices.

21. The method of claim 19, wherein the redirecting step further comprises reflecting said infrared light off of an angled surface.

22. The method of claim 19, wherein the redirecting step further comprises reflecting said infrared light off of a polished angled surface.

23. The method of claim 19, wherein the redirecting step further comprises reflecting said infrared light off of a silvered angled surface.

24. The method of claim 19, wherein the redirecting step further comprises refracting said infrared light off of a boundary region between said illumination ring and air.

25. The method of claim 19, wherein said reflected and scattered light is used for measuring a percentage of body fat.

26. The method of claim 19, wherein said reflected and scattered light is used for measuring a percentage of body water.

27. The method of claim 19, wherein said reflected and scattered light is used for measuring a percentage of muscle.

28. The method of claim 19, wherein said reflected and scattered light is used for measuring a pulse rate.

29. The method of claim 19, wherein said reflected and scattered light is used for measuring blood analytes.

* * * * *